United States Patent
Von Rheinbaben et al.

(10) Patent No.: US 6,517,852 B1
(45) Date of Patent: Feb. 11, 2003

(54) DISINFECTION METHOD

(75) Inventors: Friedrich Von Rheinbaben, Duesseldorf (DE); Holger Biering, Grevenbroich (DE); Klaus-Peter Bansemir, Langenfeld (DE)

(73) Assignee: Ecolab GmbH Co. OHG, Duesseldorf (DE)

( * ) Notice: Subject to any disclaimer, the term of this patent is extended or adjusted under 35 U.S.C. 154(b) by 0 days.

(21) Appl. No.: 09/402,407

(22) PCT Filed: Mar. 26, 1998

(86) PCT No.: PCT/EP98/01785

§ 371 (c)(1),
(2), (4) Date: Nov. 12, 1999

(87) PCT Pub. No.: WO98/44800

PCT Pub. Date: Oct. 15, 1998

(30) Foreign Application Priority Data

Apr. 4, 1997 (DE) .......................... 197 13 850

(51) Int. Cl.⁷ .................... A01N 25/00; A61K 31/155
(52) U.S. Cl. .................. 424/405; 514/634; 514/635
(58) Field of Search .................. 424/405; 514/635, 514/634

(56) References Cited

U.S. PATENT DOCUMENTS 5,017,617 A * 5/1991 Kihara et al. ............... 514/635

FOREIGN PATENT DOCUMENTS

| DE | 42 05 828 A1 | 9/1993 |
| DE | 42 21 743 A1 | 1/1994 |
| EP | 0 707 794 | 4/1996 |
| JP | 7 298862 | 11/1995 |
| WO | WO95/12395 | 5/1995 |

OTHER PUBLICATIONS

CAPLUS Abstract, AN 1977:165776, 1977, Davies et al.*
CAPLUS Abstract, AN 1971–434431, 1971, Derbyshire et al.*
Patent Abstract of Japan, vol. 096, No. 003, (1996).
Journal of Food Protection, vol. 47, No. 11, XP002073801 (1984).
Jap. Ass. Infect. Dis., vol. 55, pp. 355–366 (1981).
Zbl. Hyg., 189, pp. 554–562 (1990).

* cited by examiner

Primary Examiner—Russell Travers
Assistant Examiner—Shengjun Wang
(74) Attorney, Agent, or Firm—Merchant & Gould P.C.

(57) ABSTRACT

In order to disinfect objects at low temperatures, which can lie well below 0 ° C., said objects are treated with a hydroalcoholic solution containing an active microbicidal chlorhexidine compound. The Method enables quick reduction of germs even at low temperatures and displays a wide-ranging degree of efficacy.

12 Claims, No Drawings

DISINFECTION METHOD

This application is a 371 of PCT/EP98/01785 titled Mar. 26, 1998, which claim foreign priority of FED REP GERMANY 1971385, titled Apr. 4, 1997.

BACKGROUND OF THE INVENTION

This invention relates to a process for disinfecting articles at low temperatures using liquid microbicidal preparations.

The effectiveness of conventional chemical disinfectants is dependent not only on the contact time and concentration, but also to a large extent on the contact temperature. Studies in this field have been conducted inter alia by P. Gelinas et al. (see Journal of Food Production, Vol. 47, No. 11, pages 841–847 (1984)) and by N. Noda et al. (see J. Jap. Ass. Infect. Dis., Vol. 55, 355–366 (1981)) who describe inter alia the disinfecting effect of chlorhexidine salts and alcohols. In many cases, it has also been found that the reduction in effectiveness at low temperatures cannot be reversed by higher concentrations of active substance even if this were acceptable from the toxicological point of view. Accordingly, many substances active as microbicides at room temperature are totally unsuitable as active substances for use at low temperatures. In general, only powerful oxidizing agents, such as hypochlorite and peracetic acid, can be used at temperatures of the order of 5° C. However, these active substances are also unsuitable for many applications, for example for the disinfection of sensitive materials, on account of their corrosiveness. Accordingly, efforts have long been made to find active substances or combinations of active substances that are safe and effective without any harmful side effects for the purpose of disinfection at low temperatures, more especially at temperatures below freezing point.

The present invention represents a major improvement in this field.

DESCRIPTION OF THE INVENTION

The present invention relates to a process for disinfecting articles in which the articles are treated with an aqueous alcoholic solution containing a microbicidal guanidine derivative at temperatures below 15° C. and preferably at temperatures below 5° C. The treatment is even effective at temperatures of 0° C. or lower, in most cases at temperatures below −10° C. and even at temperatures below −50° C.

It is particularly worth mentioning that the process according to the invention is effective against not just a few, but also against a very broad spectrum of microorganisms or viruses at the in-use temperatures. In addition, the disinfection process according to the invention is extremely kind to materials and the alcoholic aqueous solutions used for disinfection retain their effectiveness even after long periods of storage.

The process according to the invention may be applied on the one hand to articles which, by their nature, have to be kept cold and which must not be heated to room temperature or beyond with their destination in mind. Examples include the disinfection of surfaces in cold rooms, cold stores and refrigerated trucks and the disinfection of special laboratory equipment, such as refrigerated centrifuges and freezers. However, the disinfection of deep-frozen or refrigerated foods also counts as a special field in this regard. The new disinfection process is also suitable for articles which, in order to prevent material damage, should not be brought into contact with conventional disinfectants at room temperature or higher temperatures. In their case, material damage can be suppressed to a considerable extent by the new process without any reduction in the effectiveness of disinfection by carrying out the disinfection process at low temperatures.

The new process is characterized by the simultaneous presence of at least one lower alcohol and at least one microbicidal guanidine derivative in the aqueous disinfection liquid. The fact that the microbicidal effect of the aqueous alcoholic solutions does not weaken with decreasing temperature, but in some cases actually increases with decreasing temperature is extremely surprising in view of the dependence on temperature of the effect of the individual components.

The guanidine derivatives suitable for use in the process according to the invention are compounds which contain a guanidine or giguanidine group one or more times in the molecule either in the form of the fre bases or in the form of the salts. Examples of such compounds are N-dodecyl-N'-methyl guanidine acetate, N-octadecyl guanidine acetate, N-alkylpolymethylene-α,ω-diguanidines (for examle Dodigen® 180, Lonzabac® GA) and polyhexamethylene biguanide hydrochloride (Lonzabac® B6, Vantocil® IB). Particularly preferred guanidine derivatives are chlorhexidine and its salts. The salts are salts of the base 1,6-di-(4-chlorophenyldiguanido)-hexane with inorganic or organic acids. Instead of the short name chlorhexidine, other names have also been used for the free base although they have not been adopted to the same extent. Guanidine derivatives or salts which are soluble in the water/alcohol mixture, even at the desired low in-use temperatures, are used in accordance with the invention. These salts may be mono- or polybasic salts. Examples of suitable salts of chlorhexidine are the dihydrochloride, the diacetate and—in a particularly preferred embodiment—the digluconate. Mixtures of several guanidine compounds or salts may of course also be used.

The concentration of guanidine compound in the solutions is normally not more than about 5% by weight although this concentration may of course be exceeded in individual cases. Concentrations of about 0.05% by weight to about 1% by weight are preferred, concentrations of about 0.01% by weight to about 0.5% by weight being particularly preferred.

The alcohols used in the disinfecting solutions are primarily lower water-miscible alcohols, more particularly aliphatic monoalcohols, although it is also possible to use glycols and other liquid polyols and partial ethers thereof, for example ethylene glycol, propylene glycol, glycerol, butoxy-ethanol and methoxybutanol. Readily volatile alcohols, more especially alcohols containing 1 to 4 carbon atoms in the molecule, are particularly preferred, ethanol and n-propanol being most particularly preferred. Instead of individual alcohols, mixtures of two or more alcohols may of course also be used. Relatively small quantities of aliphatic alcohols, which have only limited solubility in water, may also be used in admixture with water-miscible alcohols. The concentration of alcohols in the disinfecting solution should preferably be from about 40 to about 98% by weight, based on the disinfecting solution as a whole. Alcohol concentrations of about 60 to about 90% by weight and, more particularly, about 70 to about 80% by weight in the disinfecting solution are particularly preferred.

Particularly in cases where they are to be used for disinfection at or above room temperature, the aqueous alcoholic chlorhexidine solutions used in accordance with the invention may also contain other microbicides or virucides which are known to be suitable for use at such temperatures. These other microbicides or virucides include in particular quaternary ammonium compounds, hydrogen peroxide and other peroxidic compounds, aldehydes, phenols, aromatic alcohols, such as phenoxy-ethanol, and inorganic acids. These active substances are used in the usual concentrations. In general, there is no danger of their disrupting the effect of the process according to the invention at low temperatures.

In addition, the disinfecting solutions used in accordance with the invention may contain the auxiliaries and additives generally present in aqueous disinfecting solutions providing they do not impair the effect of the process in any way. Examples of such auxiliaries and additives are wetting agents, hydrotropes, surfactants, corrosion inhibitors, dyes and fragrances. The concentrations in which they used are determined by the desired effect.

The preparation of the disinfecting solution does not present any problems. In general, the chlorhexidine salt is first dissolved in alcohol in the quantity necessary for the required concentration, after which the necessary quantity of water is mixed in. If appropriate for faster dissolution, the disinfecting solution may even be prepared at elevated temperatures. Other additives are generally added last to the solutions, although they may even be pre-dissolved in the initially purely alcoholic solution or in water.

The treatment of the articles in the actual disinfection process is carried out, for example, by immersing the articles for a predetermined time in the cooled disinfecting bath or by applying the disinfecting solution to the cold articles, for example by spraying, brush-coating or by wiping the articles with an absorbent material impregnated with the disinfecting solution. The disinfecting solution may be applied to the articles both in pre-cooled form or, preferably, without cooling. The uncooled articles may also be treated with the disinfecting solution at around room temperature and then cooled with the adhering solution to the disinfection temperature over the contact time should this particular procedure appear appropriate for certain reasons, for example to prevent material damage. After disinfection, the disinfectant can be suitably removed from the articles. In many cases, however, there is no need to remove the disinfectant where residues of the disinfectant in or on the articles can be tolerated.

EXAMPLES

The microbicidal effect was tested both at room temperature (comparison) and at −20° C.

The virucidal activity was tested in accordance with the guidelines of the Bundesgesundheitsamt und die Deutsche Vereinigung zur Bekämpfung der Virukrankheiten (Zbl. Hyg. 1990: 189, 554–562), i.e. by the virus suspension test. To carry out the test, the disinfectant was mixed with the particular test virus suspension in a ratio of 9:1 and, at the end of the test period, a sample was removed from the mixture for virus titration. In cases where the suspension test was carried out with an additional protein challenge, the mixing ratio was 8:1:1 (disinfecting solution:protein solution: virus suspension).

The following virus suspensions were used:

Polio virus type 1, strain Mahoney (grown and titrated on Rhabdomyosarcoma cells)

Adeno virus type 2, strain Adenoid 6 (grown and titrated on Hela cells)

Herpes simplex virus, type 1 (grown and titrated on Vero cells) Vaccinia virus (grown on Vero cells)

Simian virus 40, strain 777 (grown and titrated on $CV_1$ cells).

In every case, the disinfecting solution and the virus suspension were mixed at room temperature (total volume 100 microliters) in Eppendorf vessels. Immediately afterwards, the test tubes were suddenly cooled to the contact temperature by immersion in a cooling bath. After the designated contact time at that temperature, the samples were reheated to room temperature. Virus detection was then carried out by microtitration using the above-mentioned cell lines after a dilution series corresponding to the progression 1:10, 1:100, 1:1000 etc. had been prepared.

The microbicidal activity of the composition used in accordance with the invention was tested by the suspension test as specified in the Richtlinie für die Prüfung und Bewertung chemischer Desinfektions-verfahren, 12.07.1991, published by the Desinfektionsmittel-Kommission der Deutschen Gesellschaft für Hygiene und Mikrobiologie (DGHM) (mhp-Verlag, Ostring 13, 6200 Wiesbaden). The following test organisms were used:

| *Staphylococcus aureus* | ATCC | 6538 |
|---|---|---|
| *Pseudomonas aeruginosa* | ATCC | 15442 |
| *Mycobacterium terrae* | ATCC | 15755 |
| *Candida albicans* | ATCC | 10231 |
| *Aspergillus fumigatus* | | |

The test surfaces used were 2×2 cm steel plates fixed to Styropor plates by sunken magnets. The surfaces were contaminated with 10 µl of germ suspension uniformly applied to the plate. The germ carriers were then stored for ca. 20 minutes at −20° C. (in a cryostat) before quantities of 0.2 ml of the disinfecting solution to be tested were applied and rubbed in with a glas spatula. After the designated contact times, the germ carriers were separated from the magnet and introduced into nutrient solutions containing de-inhibitor. The colony-forming units (CFUs) were recovered by the van Klingeren method (see Richtlinien der DGHM, 12.07.1991)

The following Table shows the test results obtained at different temperatures and with different contact times. The figures indicate in logarithmic units ($\log_{10}$) the reduction factors for the content of microorganisms and viruses after the particular contact times.

The test results show that the aqueous alcoholic chlorhexidine solution used in accordance with the invention retains a broad action spectrum even far below the freezing point.

TABLE

Virucidal and microbicidal activity

| No. | Formulation | Temp. in °C. | Virus/test germ | RF/CT 5 mins. | RF/CT 10 mins. | RF/CT 15 mins. |
|---|---|---|---|---|---|---|
| 1 | 0.2 g chlorhexidine digluconate 90.0 ml ethanol (96%) dist. water to 100 ml | −20 −20* −20** −20 | Polio | 4.4 4 3.9 | 4.4 4 >4.5 | 4.4 4 4.4 |
| | | −20 −20* −20** | HSV. | >4 >4 >4 | >4 >4 >4 | >4 >4 >4 |
| | | −20 −20* −20** | Vacc. | >4 >4 >4 | >4 >4 >4 | >4 >4 >4 |
| | | −20 −20* −20** | SV 40 | >3.5 >3.5 >3.5 | >3.5 >3.5 >3.5 | >3.5 >3.5 >3.5 |
| | | −20 | Staph. aureus | 5.26 | 5.70 | 5.81 |
| | | −20 | Pseud. aerug. | 5.58 | 5.60 | 5.48 |
| | | −20 | Myc. terrae | 4.35 | 5.48 | 5.23 |
| | | −20 | Cand. alb. | 4.54 | 5.02 | 5.36 |
| | | −20 | Asperg. fumig. | 4.35 | 5.50 | 5.62 |
| 2 | 74.5 ml ethanol (96%) dist. water to 100 ml | RT −20 | Polio | 0.4 0 | 0.7 0 | 0.7 0 |
| | | RT −20 | SV 40 | 1.2 1.3 | 1.4 1.4 | 2.1 1.5 |

**Addition of foetal calf serum
**Addition of bovine serum albumin
Abbreviations:
CT: contact time
RF: reduction factor
RT: room temperature

What is claimed is:

1. A process for disinfecting an article in need thereof, comprising:
   contacting the article with an aqueous solution at less than 0° C.;
   the aqueous solution comprising an alcohol and 0.01 to 0.5 wt-% of a microbicidal chlorhexidine compound.

2. The process of claim 1, wherein the chlorhexidine compound comprises chlorhexidine dichloride, chlorhexidine diacetate, chlorhexidine digluconate, or mixture thereof.

3. The process of claim 2, wherein the chlorhexidine compound comprises chlorhexidine digluconate.

4. The process of claim 1, wherein the alcohol comprises one or more $C_1$ to $C_4$ alcohols.

5. The process of claim 4, wherein the alcohol comprises ethanol, n-propanol, or mixture thereof.

6. The process of claim 1, wherein the solution comprises 40 to 98 wt-% of the alcohol.

7. The process of claim 6, wherein the solution comprises 60 to 90 wt-% of the alcohol.

8. The process of claim 7, wherein the solution comprises 70 to 80 wt-% of the alcohol.

9. The process of claim 1, comprising contacting the article with the solution at less than −10° C.

10. The process of claim 9, comprising contacting the article with the solution at less than −50° C.

11. A process for disinfecting an article in need thereof, comprising:
    contacting the article with an aqueous solution at less than 0° C.;
    the aqueous solution comprising:
        40 to 98 wt-% of a $C_1$ to $C_4$ alcohol; and
        0.01 to 0.5 wt-% of chlorhexidine dichloride, chlorhexidine diacetate, chlorhexidine digluconate, or mixture thereof.

12. The process of claim 11, wherein the aqueous solution comprises 60 to 90 wt-% ethanol, n-propanol, or mixture thereof.

* * * * *